United States Patent
Bernstein (10) Patent No.: US 7,041,051 B2
(45) Date of Patent: May 9, 2006

(54) AUTOMATED SELF-PROPELLING ENDOSCOPE

(75) Inventor: Lionel M. Bernstein, 1802 Kalorama Square, NW., Washington, DC (US) 20008

(73) Assignee: Lionel M. Bernstein, Washington, DC (US)

( * ) Notice: Subject to any disclaimer, the term of this patent is extended or adjusted under 35 U.S.C. 154(b) by 246 days.

(21) Appl. No.: 10/474,518

(22) PCT Filed: Apr. 26, 2002

(86) PCT No.: PCT/US02/11857

§ 371 (c)(1),
(2), (4) Date: Oct. 23, 2003

(87) PCT Pub. No.: WO02/087495

PCT Pub. Date: Nov. 7, 2002

(65) Prior Publication Data

US 2004/0260150 A1 Dec. 23, 2004

Related U.S. Application Data

(60) Provisional application No. 60/290,658, filed on May 15, 2001, provisional application No. 60/286,366, filed on Apr. 26, 2001.

(51) Int. Cl.
*A61B 1/00* (2006.01)
(52) U.S. Cl. ........................ 600/114; 600/146
(58) Field of Classification Search ............... 600/114, 600/115, 118, 146; 606/108; 604/95.01, 604/156
See application file for complete search history.

(56) References Cited

U.S. PATENT DOCUMENTS

| | | |
|---|---|---|
| 4,054,128 A | 10/1977 | Seufert et al. |
| 4,066,071 A | 1/1978 | Nagel |
| 4,389,208 A | 6/1983 | LeVeen |
| 4,561,427 A | 12/1985 | Takada |
| 4,991,957 A | 2/1991 | Sakamoto et al. |
| 5,353,807 A | 10/1994 | DeMarco |
| 5,482,029 A | 1/1996 | Sekiguchi et al. |
| 5,586,968 A | 12/1996 | Grundl et al. |
| 5,645,520 A | 7/1997 | Nakamura et al. |
| 5,662,587 A | 9/1997 | Grundfest et al. |
| 5,759,151 A | 6/1998 | Sturges |
| 5,819,736 A | 10/1998 | Avny et al. |
| 5,906,591 A | 5/1999 | Dario et al. |
| 5,916,146 A | 6/1999 | Allota |
| 5,984,860 A | 11/1999 | Shan |
| 5,996,346 A | 12/1999 | Maynard |
| 6,077,219 A | 6/2000 | Viebach et al. |
| 6,162,171 A | 12/2000 | Ng |
| 6,293,907 B1 | 9/2001 | Axon |
| 6,309,346 B1 | 10/2001 | Farhadi |
| 6,315,713 B1 | 11/2001 | Takada |
| 6,332,865 B1 | 12/2001 | Borody |

*Primary Examiner*—Beverly M. Flanagan
(74) *Attorney, Agent, or Firm*—Edell, Shapiro & Finnan, LLC

(57) ABSTRACT

An improved mechanism for an automated self-propelling endoscope. The system augments the conventional "proximal-push" mechanism commonly used in colonoscopy with an innovative "distal-pull" mechanism. The distal-pull mechanism includes external application of a force at the proximal end of the endoscope that is translated into force that is exerted upon and moves the distal (leading) end of the scope further into the colon.

27 Claims, 8 Drawing Sheets

AUTOMATED SELF-PROPELLING ENDOSCOPE

CROSS REFERENCE TO RELATED APPLICATIONS

This application claims priority from U.S. Provisional Patent Application Ser. Nos. 60/286,366, entitled "Mechanism For Automated Self-Propelling Endoscope," filed Apr. 26, 2001, and 60/290,658, entitled "Improved Mechanism For Automated Self-Propelling Endoscope," filed May 15, 2001. The disclosures of these provisional patent applications are incorporated herein by reference in their entireties.

BACKGROUND OF THE INVENTION

1. Technical Field

The present invention relates to an improved mechanism for an automated self-propelling endoscope.

2. Discussion of the Related Art

The flexible fiberoptic colonoscope has provided direct visualization of the inner surface of the entire colon, and has greatly influenced the diagnosis and treatment of colonic diseases over the past three decades. It is pervasively used throughout the U.S. and much of the industrialized world. It provides information that is complementary to common radiologic, CT scan, MRI, and other sophisticated imaging scanning techniques in the diagnosis of colonic disease, and in many circumstances it is considered to provide the most reliable, efficient and effective available tool. Via instruments inserted through channels in the scope, a wide array of diagnostic and therapeutic instruments can be used. However, a major impediment to colonoscopy is the long time that often is required to examine the full length of the colon. The introduction of the scope is in a direction opposite to that effected by normal peristaltic waves. Further, the tubular colon is tortuous and highly flexible, and its walls often fail to direct and guide the scope as it is moved into the colon. As the scope is manually propelled, it enters loops of colon that become "cul-de-sacs" which trap the leading end of the scope, and prevent the desired retrograde movement of the scope through the lumen. Advancing the scope is reminiscent of attempts to "push a chain or a flexible rope". With only manual insertion efforts, progression of the distal end of the scope into the colon is successful for the first few short distances; but as the length of penetration increases and tortuous configurations of bowel need to be negotiated, the difficulties increase greatly, even with visual directional guidance of the tip of the scope. The endoscopist uses a variety of maneuvers to nudge the scope further, including repeatedly repositioning the patient (and the colon); utilizing gravity effects to move the heavier leading end of the scope "downhill"; manipulating the scope against the bowel wall to round corners; applying pressure on the external abdomen; altering the rigidity of segments of the scope to more effectively translate push-effects distally; changing lumen size and configuration with air insufflation; etc. However much endoscopists do succeed in traversing the entire colon, there is clearly need for mechanisms to facilitate the process and to hasten its accomplishment. Many examinations require much time, and many are terminated before the examination is complete. Thus, a mechanized process that would allow rapid retrograde propelling of the scope to the cecum would be of great value. Colonoscopic examinations are costly, and part of this is due to the amount of professional time required for the complete examination. In summary, were an automated mechanism available to facilitate rapid traversal of the colon, it would increase both the effectiveness and efficiency of the wide range of diagnostic and therapeutic uses of the procedure, and contribute to reducing the financial cost of the procedure.

The essence of the problem is to develop a mechanized propelling system that is self-contained in the instrument that does not depend upon the external guidance effect of the surrounding highly flexible tubular bowel. Force to insert the colonoscope through the anus into the patient is simple and straightforward. What is needed is some array of technology that would simulate the actions of a "virtual hand" that was located in the lumen of the colon just ahead of the tip of the endoscope, and could grasp and pull the tip in the direction of the lumen toward the proximal colon. This is akin to a "Maxwell's demon's hand" that could and would "knowingly" act as needed.

An analogous problem exists for the small bowel endoscope (enteroscope). The small bowel is about 30 feet long and telescopes itself on introduced instruments. It may take several hours for an enteroscope to traverse major portions of the small bowel. As a result, this is a rarely used procedure.

Some characteristics of a conventional fiberoptic endoscope (colonoscope) are as follows: the scope is flexible in all directions along its central or longitudinal axis; it has a length of about 164 cm and a diameter of about 14.2 mm; the scope includes a fiberoptic viewing channel and fiberoptic light pipes, and a depth of focus of about 5–100 mm; controllable tip deflection of the scope is 180°/180° up/down and 160°/160° right/left; and one or more air and water delivery channels provided in scope. In addition, a conventional scope typically includes one or more open channels for insertion of instruments for suction, biopsy, surgical incisions, injections, sonography, laser therapy, etc.

For reasons of safety, comfort to patients, and reduction of time and costs of colonoscopic (and enteroscopic) procedures, a system which would allow automated retrograde introduction of endoscopes that followed the course of the bowel lumen would be highly beneficial. When fully introduced in a timely fashion, existing fiberoptic colonoscopes are remarkably effective instruments for a variety of diagnostic and therapeutic interventions. Over the past two decades, commercial developments have produced small incremental improvements in the endoscopes and the instruments that are fed through their channels. The one major innovation over recent years has been the introduction of scopes by the Olympus Corporation that allows for selective increases of rigidity of its segments; this has been demonstrated (Brooker, J. C. et al.: Gut; June, 2000: 46:801–805) to be very helpful to the "proximal-push" mechanism which has been and presently remains the main mode for state-of-the-art propulsion of endoscopes. Nonetheless, many investigators have recognized continuing need for and have attempted to augment the proximal-push forces with other means to facilitate delivering the endoscope to the entire target area.

The related art reveals a variety of approaches that have been taken to improve the safety, efficacy, comfort, and efficiency of colonoscopy. Examples of some different approaches to enhance the design of an endoscope can be seen in U.S. Pat. Nos. 4,054,128, 4,389,208, 4,991,957, 5,353,807, 5,482,029, 5,645,520, 5,662,587, 5,759,151, 5,819,736, 5,906,591, 5,916,146, 5,984,860, 5,996,346, 6,162,171, 6,293,907, 6,309,346, 6,315,713 and 6,332,865. The disclosures of these patents are incorporated herein by reference in their entireties. The efforts to deliver the working end of endoscopes to the sites required for complete examination or treatment of the colon and small bowel have included several different modalities for physically transporting the endoscope into the patient. Yet, the clinical state-of-the-art for colonoscopy has rested on the decades old "proximal-push technology" as its mainstay, with the recent major improvement offered by introduction of scopes by the Olympus Corporation that allow for selective increases of rigidity of its segments. Otherwise, technical improvements of colonoscopes themselves have been small and incremental; nonetheless, the net result of the numerous small improvements over the years is the current availability of colonoscopes that are technical marvels. Illumination and visual fields; flexibility of the body; universal flexible directional control of the distal end of the scope; air and water jet delivery channels; one or more small to large channels for insertion of instruments to provide suction, biopsy, injections, incisions, sonography, laser therapy, etc., etc. attest to the great versatility and effectiveness of this modality in management of gastrointestinal disease. Indeed, the proliferation of many sophisticated instruments which are introduced via the scope's channels has so greatly increased the usefulness of colonoscopy that the lack of more major improvements in its own intrinsic technology has been comfortably tolerated.

What are the important improvements in current state-of-the-art colonoscopy that cry out for attention and solution? Mostly they revolve about the ease, comfort, safety and rapidity of introduction and traversing of the entire colon for the intended diagnostic and/or therapeutic purposes. By synthesizing the information in the many patents listed above, the following points can be observed:

1. Major efforts have been expended and are under way to devise innovative methods for transporting the endoscope to where it needs to be with appropriate control, timeliness, safety, ease and comfort; this confirms the importance of these continuing needs.

2. The proximal-push mechanism is central and necessary for propelling a colonoscope, but it is not fully sufficient. Many investigators have deliberately attempted to augment the proximal-push with other forces to propel the colonoscope to meet the described needs.

3. It is becoming progressively more difficult to clearly identify the boundaries between technical support of medical/surgical clinical gastroenterology and the robotics supporting minimally invasive surgery (MIS).

4. In the attempts to innovate more effective endoscopic instruments, some investigators have developed instruments that come to look less and less like current endoscopes. Many have substituted new complicated technologies that are not superior to current colonoscopes to supplant existing scopes rather than creating new systems that can utilize the very mature, superb existing scopes. Many proposals rely on moving parts gaining traction against the bowel wall, or pushing on the wall, or that use pneumatic suction to adhere to the wall, all of which may alter or injure the mucosa. Others significantly increase the bulk of instruments that are inserted into the colon.

From these disparate considerations, a new vision crystallized: An improved propelling mechanism for the colonoscope should not sacrifice any meaningful characteristics of today's state-of-the-art colonoscope. This dictates that an innovative propelling mechanism must be engrafted upon today's existing scopes; an innovative propelling mechanism should be implemented which requires no or relatively few structural changes of existing colonoscopes, where any changes are so minimal as not to disturb any of their present attributes.

SUMMARY OF THE INVENTION

Accordingly, it is an object of the present invention to provide an improved mechanism for an automated self-propelling endoscope ("scope") that is highly effective in propelling the scope within the bowels.

Another object of the present invention is to provide a highly effective self-propelling endoscope with minimal alteration to the scope design.

A further object of the present invention is to provide a propelling mechanism for the scope that enhances the classical "proximal-push" mechanism conventionally utilized in the colonoscope art.

The aforesaid objects may be achieved individually and/or in combination, and it is not intended that the present invention be construed as requiring two or more of the objects to be combined unless expressly required by the claims attached hereto.

According to the present invention, a self-propelling endoscope system is established that is capable of converting a colonoscope into an automated self-propelling colonoscope. In particular, the system of the present invention is capable of converting a standard, unmodified commercial colonoscope into an automated self-propelling colonoscope with no (or minimal) alteration to the colonoscope itself.

The system augments the classical "proximal-push" mechanism with a "distal-pull" mechanism. The proximal-push mechanism consists simply of serial insertions of lengths of the scope through the anus into the patient. The distal-pull mechanism ultimately consists of externally applying force at the proximal end of the scope that is translated into force that is exerted upon and moves the distal (leading) end of the scope further into the colon. This force translation includes: 1) controlled anchoring of the loop of the scope between sites at the proximal operating end, and immediately external to the anus; 2) an inserted flexible wire obturator having an external wall releasable connector (e.g., a circumferential inflatable balloon) located just proximal to the scope's flexible leading segment to temporarily bond the leading end of the obturator with the leading end of the body of the scope; and 3) stationary racks with couplings which grasp and either hold stationary, or electromechanically move the scope body through the anus into the colon, and in controlled sequence apply the moving force to the proximal end of the obturator. Various combinations and sequences of these actions result in specific patterns of scope locomotion that, when integrated and cyclically repeated, facilitate the automated self-propelling mechanism for the endoscope. In other embodiments, minor modifications of the colonoscope provide other mechanisms accomplishing the propelling mechanism. All propelling movements, as described in detail below, may also be performed manually by assistants to the endoscopist.

The above and still further objects, features and advantages of the present invention will become apparent upon consideration of the following definitions, descriptions and descriptive figures of specific embodiments thereof wherein like reference numerals in the various figures are utilized to designate like components. While these descriptions go into specific details of the invention, it should be understood that variations may and do exist and would be apparent to those skilled in the art based on the descriptions herein.

DESCRIPTION OF THE PREFERRED EMBODIMENTS

In an exemplary embodiment of a self-propelling endoscope system of the present invention includes modification of existing flexible obturators, and use of external automated controlling mechanisms, but requires no modification of the endoscope itself. Other embodiments involve slight modification to the endoscope as described below.

Figures 1A, 1B:
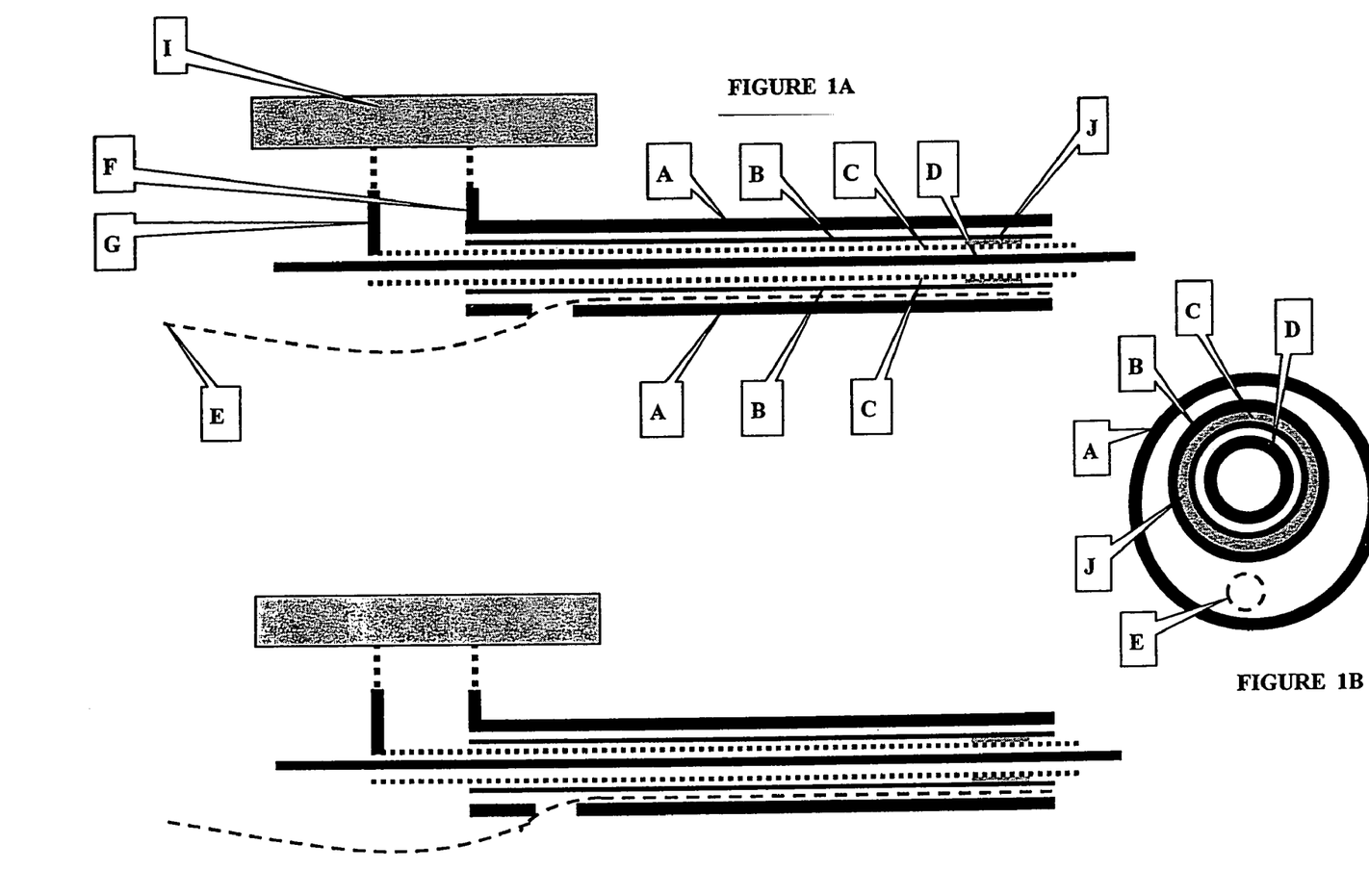
FIG. 1A is an elevated side view in partial section of a self-propelling endoscope system according to the present invention.
FIG. 1B is a cross-sectional view taken along lines 1B—1B of the endoscope of FIG. 1A.

FIGS. 1A and 1B illustrate schematic sagittal (i.e., longitudinal cross-section) and cross-sectional views of the endoscope. The sagittal section depicts a flexible colonoscope laid out in a linear fashion. Its essential components are labeled and shown in FIG. 1A. FIG. 1B is a schematic cross-sectional view. Letters "A" through "J" are labels to identify the following components:

A). Outer wall of colonoscope.

B). Wall of "obturator channel" forming the lumen (diameter preferably in the range of about 3.8–5 mm) through which wire obturators are passed. The obturator channel wall is integrally attached to the outer wall of the colonoscope such that movement of the obturator channel wall forces corresponding movement of the scope. To allow clarity of illustration, the size of this channel is greatly exaggerated relative to the cross-section of the remaining parts of the endoscope. During the automated propelling phase, this channel contains the inserted obturators whose manipulations effect the forward movement of the endoscope. However, after the scope has been fully introduced, these obturators are withdrawn, and the full channel is available for suction or for insertion of any of the numerous diagnostic and therapeutic tools available.

C). Wall of outer coiled wire obturator or EXT-obturator, illustrated as a dotted line. The EXT-obturator is highly flexible along its linear axis, it is non-distensible, and its total length is negligibly expandable or compressible. It is the vehicle mediating the propelling system described in detail below. Its distal end protrudes beyond the distal end of the scope into the colon, and can serve as a suction channel throughout the procedure.

D). Wall of inner coiled wire obturator or INT-obturator, illustrated as a solid line. It also is highly flexible along its linear axis, is non-distensible, and its length neither expandable nor compressible. Of the two obturators used in the propelling system, the INT-obturator has the smaller diameter, and is inserted through the lumen of the EXT-obturator. As seen in the cross-sectional view of FIG. 1B, the INT-obturator has a lumen that can be used for additional optional suction during the propelling phase. It has no role in the propelling mechanism, and, optionally, may not be included during propelling of the scope as described below. The lumen of the INT-obturator is not depicted in FIG. 1A; rather, the INT-obturator is represented as one single wide line to facilitate visualizing the relationships between the two obturators.

E). Fiberoptic channel and other functional components. Together, all of these components are rendered as a single dashed line in the figures. The fiberoptic channel is located in the space within the colonoscope's outer wall, and is external to the obturator channel. The several other functional elements that are similarly located in this space which are not separately depicted graphically are represented by this same dashed line; included are channels for fiberoptic light-pipes; guide-wires for universal directional flexing of the leading tip of the scope; air inflation; and water inflation. Together, these "E" elements make up the bulk of the cross-sectional content of the endoscope. Consider all of these elements as a bundle that constitutes the major operating end of the scope held by the endoscopist. The "E" bundle is separated from the obturator channel and its contents near the proximal end of the scope. The curved pathway of the dashed line is meant to convey the physical separateness and mobility of the operating end of the scope, so that the endoscopist can integrate and control the usual tasks with those associated with the automated propelling operation. To facilitate description of the system, the size of the obturator channel and its contents is grossly exaggerated in the figures, and the proximal end of the obturator channel is depicted in straight continuity with the remaining portion throughout the length of the scope. However, the obturator channel may include other configurations (e.g., this channel typically includes a small side channel coming off of the larger body of the endoscope).

F). Flange secured to the proximal end of the scope and the proximal end of the obturator channel. This flange, when grasped and held in a fixed position by a coupling mechanism (dotted line) of Rack One (I) stabilizes the spatial position of the proximal end of the automated propelling mechanism.

G). Flange secured to the proximal end of the EXT-obturator. This flange, when grasped and held in a fixed position by another coupling mechanism (dotted line) of Rack One, controls the movement of the EXT-obturator. A motor within Rack One exerts intermittent controlled timing of controlled variable force on the flange to move the EXT-obturator forward (i.e., from left to right in FIGS. 1A and 1B) or backward (i.e., from right to left in FIGS. 1A and 1B).

Since the INT-obturator serves as an optional suction conduit, the operator may choose to manually control its placement and movement. If desired, an alternative is to couple the EXT-obturator and the INT-obturator to maintain a constant spatial relationship therebetween.

I). Rack One. Rack One sits upon and is strongly fastened to a platform or table (not shown) located adjacent to the proximal end of the endoscope. This stabilizes the proximal region of the scope distal to where the endoscopist holds its major operating end. Rack One has two potential coupling mechanisms attached to flanges F and G. One coupling mechanism couples to flange F and holds the obturator channel immobilized at a fixed point in space. The other coupling mechanism couples to flange G and holds the EXT-obturator and, as programmed, either holds it motionless, or as force is applied, moves the obturator forward. Rack One further includes a controller and/or other suitable components (e.g., motors or other electromechanical components) to control movement of the coupling mechanisms thereby effecting automated movement of the EXT-obturator and the obturator channel.

J). A mechanism to reversibly bond the distal end of the EXT-obturator with the distal end of the scope's channel wall. In an exemplary embodiment, this is accomplished by inflation of a circumferential cylindrical balloon on the outer wall of the EXT-obturator. (Alternatively, a series of closely adjacent smaller balloons may be used to avoid this segment of the scope losing its flexibility as the balloons are inflated).

Figure 2A:
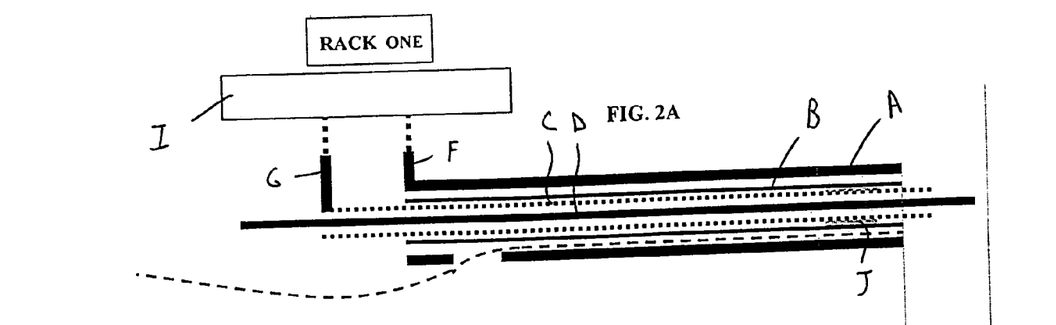
FIGS. 2A–2C are elevated side views in partial section of the system of FIG. 1A showing the "distal-pull" effect exerted from the proximal end of the endoscope.
Figure 2B:
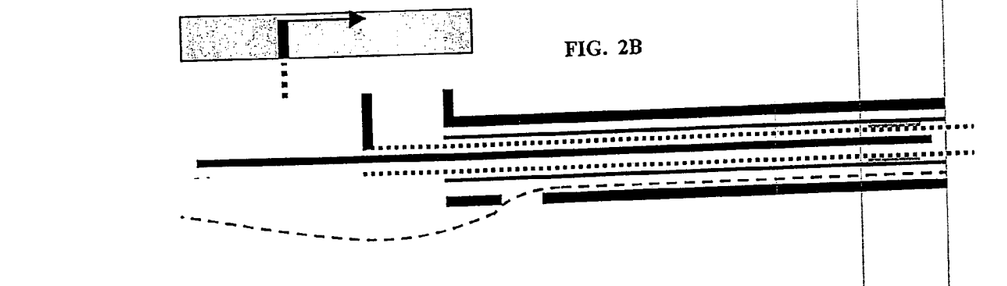
Figure 2C:
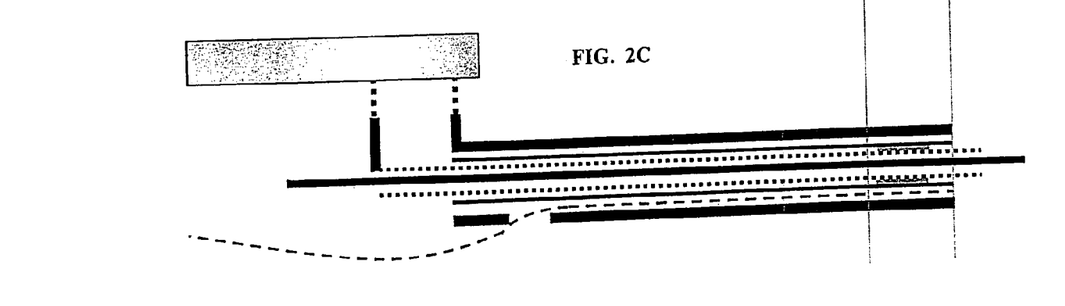

A "distal-pull" effect exerted from the proximal end of an endoscope in a simplified linear configuration model is now described in relation to FIGS. 2A–2C. FIGS. 2A–2C illustrate, in a simplified model and a linear configuration, the steps by which manipulation of the EXT-obturator can exert a distal-pull effect on a flexible endoscope. FIG. 2A shows the endoscope lying on a flat surface in a linear configuration. In FIG. 2A the two coupling mechanisms of Rack One are shown as grasping and holding stationary the proximal end flanges F and G of the obturator channel wall and the EXT-obturator, respectively. Releasable bonding of the distal ends of the EXT-obturator and the obturator channel is provided with the inflated balloon J. As previously noted, this releasable bonding may be provided with any other suitable mechanism.

In FIG. 2B, the Rack One instructions are to release the flange to the proximal end of the scope and to grasp and exert forward (i.e., left to right) force on the EXT-obturator flange, shown by the arrow in the Rack One box, to move it one unit distance. Because the distal end of the EXT-obturator is bonded to the channel wall, the forward thrust on the EXT-obturator pushes the distal end of the obturator channel forward along with the entire endoscope which is integrally attached to it. Thus, the effect is the same as manually grasping the distal end of the scope and pulling it forward (i.e., to the right as illustrated in FIGS. 2A–2C). In this linear configuration, it is easy to see that force exerted at the proximal end of the scope (i.e., on the flange of the EXT-obturator) simulates the effects of an external pulling force exerted on the distal end of the scope. To use this effect in a real-life endoscopy context, a major challenge involves devising a system in which such a "distal pull" can be effected when the scope is not in a linear configuration, but rather follows multiple curves outside the body and as it moves through the bowel. As the scope moves forward (i.e., to the right in FIGS. 2A–2C), the INT-obturator, having been held motionless, no longer protrudes beyond the distal end of the scope.

In FIG. 2C, the Rack One instructions are to hold the flanges of the proximal ends of the scope and EXT-obturator motionless, and manually the INT-obturator is moved one unit distance forward. This completes one full cycle, re-establishes the spatial relationships between the endoscope and the two obturators as illustrated in FIG. 2A, and the entire scope has been moved forward one unit distance (i.e., compare the positioning of the endoscope in FIGS. 2A and 2C).

Another embodiment of the present invention is depicted in FIGS. 3–7. This system is similar to the system of FIGS. 1–2 and includes a Rack Two K, which is similar in design and operability to Rack One. Each Rack One and Rack Two includes coupling mechanisms as described below to effect movement of the EXT-obturator C and obturator channel B as described below. This system also illustrates a "distal-pull" effect exerted from the proximal end of an endoscope in a real-life configuration involving tortuous path rather than linear movement configurations. To explain the "distal-pull" effect in this system, it is necessary to (A) describe the operational configuration of the endoscope in actual practice; (B) detail the functions of Rack One and Rack Two of the system as to their respective roles in contributing to forward (i.e., left to right as illustrated in FIGS. 3–7) motion of the endoscope; and (C) describe integration of the various components in the system to accomplish the automated propelling motion.

A. Operational Configuration of the Endoscope in Actual Practice

Figure 3:
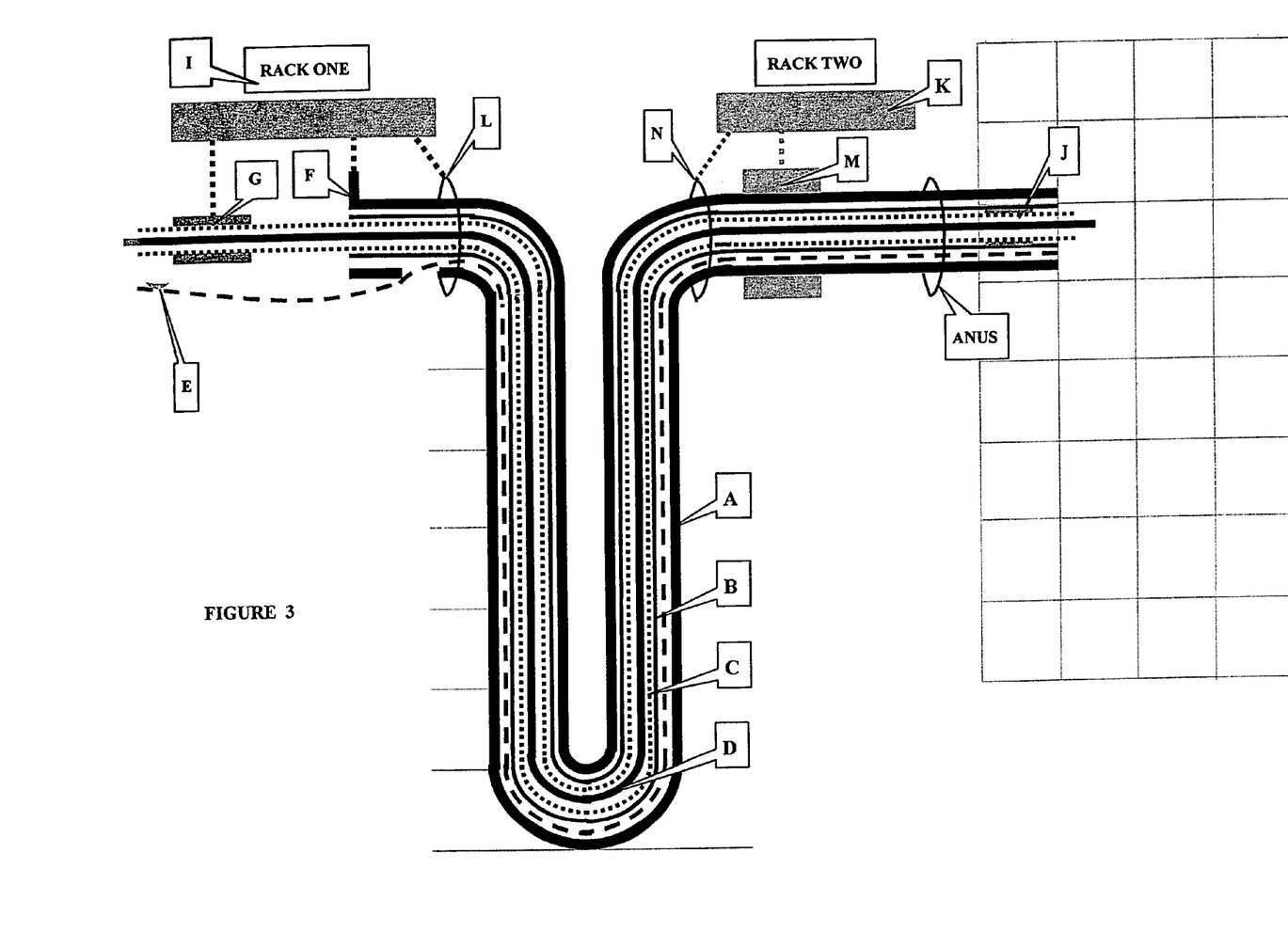
FIG. 3 is a side view in partial section of another embodiment of a self-propelling endoscope system according to the present invention.
Figure 4:
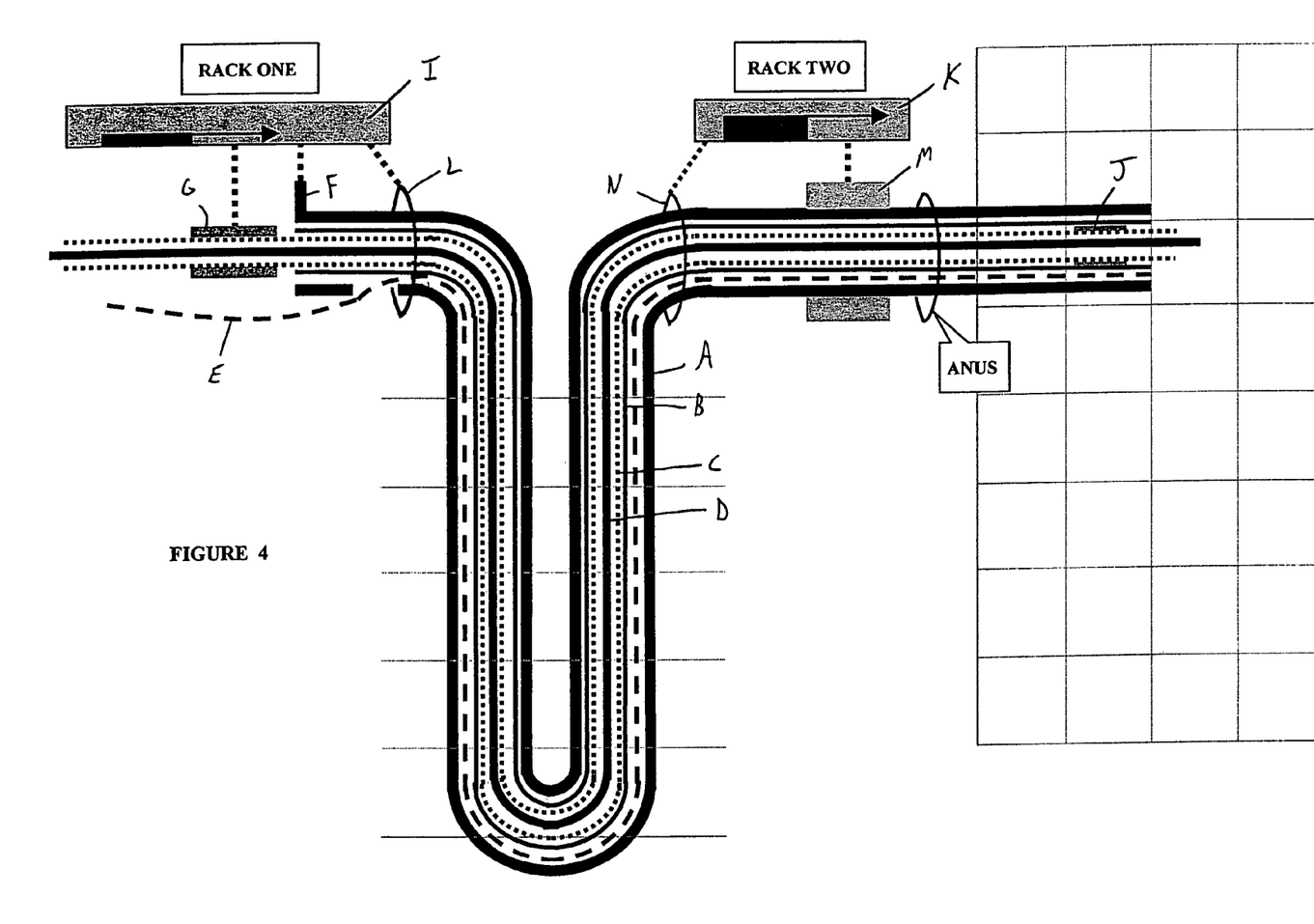
FIG. 4 is a side view in partial section of the system of FIG. 3 showing a completed cycle of strong "proximal-push" and "distal-pull" effects.

The operational configuration of the endoscope in actual practice is represented in FIG. 3. The proximal controls of the endoscope for directing the distal tip, water and air insufflation, fiberoptic light pipes, and the optical channel for visualizing the gut are bundled together (depicted as dashed line E) and held by the endoscopist. The proximal end of the obturator channel F is held in a fixed position by the Rack One coupling mechanism. This defines the beginning of a long loop formed initially between the operating proximal end of the scope and the distal end of the scope that is manually inserted through the anus into the distal colon. The stability of the proximal end of the scope is enhanced by a firm coupling to a rigid ring L through which the scope passes. The scope is also firmly coupled and firmly supported by a second ring N through which the scope passes. Operationally, the end of the loop of the scope is at the anchored point M. The rings L and N are respectively coupled (see dashed lines in FIG. 3) to Rack One I and Rack Two K.

Rack Two provides stationary stable support for the colonoscope beyond the loop by two sets of clamps, disposed at point M in FIG. 3. The two sets of clamps work alternately as described below. At all times through a cycle, one or the other of the clamp sets is holding and controlling the location of the body of the scope in this region. At the beginning and end of each cycle, one or the other set of clamps fixes the endoscope at point M. Together, the coupling mechanisms coupled to flange F and point M provide two stationary points in space at which the proximal end of the obturator channel and the immediate post-loop colonoscope are continuously anchored, allowing for complete control of the length of the loop between them, and assuring that there is no increase in the length of the loop when forces are applied to the scope. The importance of this for the propelling mechanism is described below.

Consider FIG. 3 as the baseline stage at which the endoscopist has manually advanced the endoscope under visual guidance as far into the rectosigmoid area as is practical, and where use of the automated propelling activity is then considered. The EXT-obturator is fully inserted into the scope channel. A fine plastic tube extending along its entire length allows its distally located balloon J (or other suitable bonding mechanism) to be inflated from an external position. Inflation of the circumferential balloon serves as a circumferential wedge in the space between the EXT-obturator and the obturator channel, thereby bonding the two. When the EXT-obturator is moved, it drags the distal end of the scope with it. Comparison of FIG. 4 with FIG. 3 shows the effects of one full propelling cycle. Note the limited areas of background gridlines that allow easy comparison of the movements and positions of the colonoscope and the obturators as cycles of the propelling mechanism are activated and changes are shown in sequential figures.

B. Detailed Description and Functions of Rack One and Rack Two for Propelling the Eendoscope Forward FIG. 3 depicts Rack One and Rack Two at the beginning of a propelling cycle. Rack One sits upon and is strongly fastened to a platform or table located adjacent to the proximal end of the endoscope. It has two potential coupling mechanisms, each designated by a dotted line when active. In FIG. 3, the vertical line attached to the coupling of the proximal end of the obturator channel F establishes a fixed and stable location for it; the proximal end of the obturator channel does not change its location during the entire operation of the automated propelling operation. This stability is enhanced by a similar firm coupling to rigid ring L through which the scope passes. Beyond the ring L is the loop that consists of the major length of the endoscope. The coupling mechanism at point G, including a pair of clamps, holds the EXT-obturator stationary with respect to Rack One I.

Electrical motors of Rack One provide variable controlled levels of force to be exerted on the coupling of the obturator. The critical effects of forward (i.e., left to right) force exerted on the EXT-obturator are described as follows.

Figure 5A:
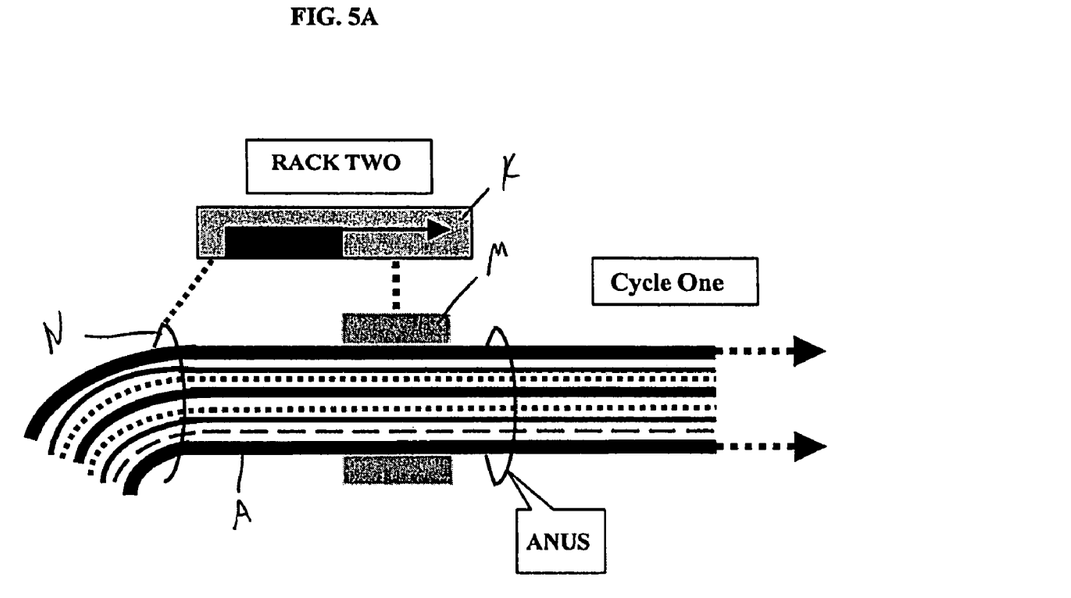
FIGS. 5A and 5B are side views in partial section of the system of FIG. 3 showing operation of the clamps at the Rack Two location of the system.
Figure 5B:
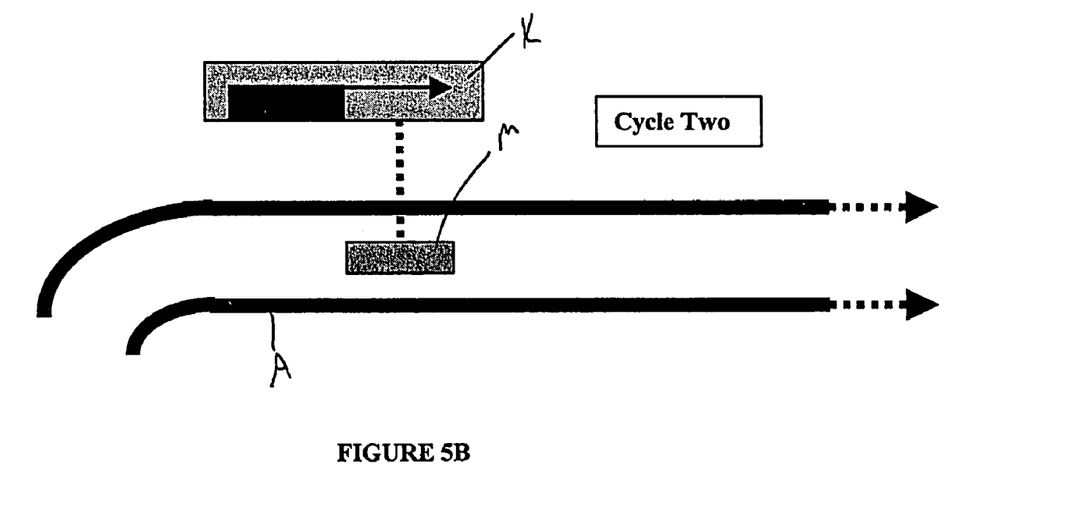

As illustrated in FIGS. 5A and 5B, Rack Two K sits upon and is strongly fastened to a platform or table located adjacent to the patient's anal insertion area. Rack Two controls two sets of alternating clamps at point M. Specifically, FIG. 5A illustrates the movements of one set of two clamps located at 12 o'clock and 6 o'clock on the circumference of the endoscope at point through the course of one time cycle. At the beginning of a first cycle, the two clamps of the first set grasp the top and bottom surfaces of the colonoscope. Force is exerted on the set of clamps, via Rack Two, to move them from the proximal, or left, to the distal, or right, position (as shown by the arrow in the Rack Two box of FIG. 5A), thereby moving the scope forward into the patient by one unit length (also indicated by dotted arrows in FIG. 5A). The clamps are released at the end of the first cycle. During the second cycle, the released clamps are returned to their original proximal position. In the third cycle, the steps of the first cycle are repeated.

FIG. 5B summarizes actions in the second cycle in which two clamps of the second set at point M, located at 3 o'clock and 9 o'clock on the circumference of the endoscope, perform similarly. That is, at the beginning of the second cycle, these two clamps grasp the two sides of the colonoscope. For purposes of convenience, the obturator channel wall, INT- and EXT-obturators and bundle of wires E are not shown in FIG. 5B. Force is applied, via Rack Two, to move these clamps from the proximal to the distal position (as shown by the arrow in the Rack Two box of FIG. 5B), thereby moving the scope forward into the patient by one additional unit length. The clamps are released at the end of the second cycle. During the third cycle, the released clamps are returned to their original proximal position. In the fourth cycle, the steps of the second cycle are repeated. Thus, the two alternating sets of clamps serve both to move the scope and to be a continuous anchor of the endoscope at point M at the end of each cycle. They provide a smooth forward motion of the scope into the patient. Variable controlled levels of force to be exerted on the sets of clamps are provided by electrical motors of Rack Two.

A similar coupling-clamp mechanism is used to move the EXT-obturator forward by force applied to its proximal end at point G (see FIG. 3), resulting in forward (i.e., left to right) motion of the scope. Because of the smaller diameter of the EXT-obturator, the two sets of clamps are mounted on adjacent serial segments rather than on different parts of the circumference of the same segment.

C. Integration of the Various Components of the System to Accomplish the Automated Propelling Motion.

In the system described above, the transit of the endoscope from the distal toward the proximal colon is effected through two sets of actions: one is the "proximal-push" effect and the other is the "distal-pull" effect. The simultaneous combined use of automated proximal-push and distal-pull mechanisms greatly facilitates rapid transit of the scope from the distal colon to the cecum.

Initially, the proximal-push effect is begun by manually inserting the scope through the anus into the rectum and pushing it into the sigmoid area. With only manual insertion efforts, progression of the distal end of the scope into the colon is successful for the first few short distances; but as the length of penetration increases and tortuous configurations of bowel need to be negotiated, the difficulties may increase meaningfully, even with visual directional guidance of the tip of the scope. The endoscopist uses a variety of maneuvers to nudge the scope further, including repeatedly repositioning the patient (and the colon); utilizing gravity effects to move the heavier leading end of the scope 'downhill"; manipulating the scope against the bowel wall to round corners; applying pressure on the external abdomen; altering the rigidity of segments of the scope to more effectively translate push-effects distally; changing lumen size and configuration with air insulation; etc. However much endoscopists do succeed in traversing the entire colon, there is clearly need for mechanisms to facilitate the process and to hasten its accomplishment.

Consider the isolated proximal-push effect of the two sets of clamps controlled by Rack Two at point M. The alternation of the two sets of clamps essentially provides a controlled automation of the usual manual insertion efforts described above. However, even using the supportive manipulations described above, successful negotiation of the entire colon by this method alone often is problematical.

Consider one cycle of activity of the propelling system in which the proximal-push effect of Rack Two is dominant and strong, and there also is a strong distal-pull effect of Rack One. Comparison of FIG. 3 as the initial state prior to the cycle, with FIG. 4 as the end of the cycle allows analysis of the interacting changes that occur. The Rack Two clamps at point M close firmly on the endoscope; left to right force is applied by the Rack Two coupling mechanism, moving the clamps one unit length from their proximal to their distal positions; and the terminal portion of the endoscope likewise is pushed one unit distance into the patient. At the end of the cycle, the second set (3 o'clock and 9 o'clock) of clamps close firmly on the scope at point M. Because points F and M are fixed in space, the one unit length of the endoscope's advance into the patient (seen on the grid) requires shortening of both the descending and ascending limbs of the loop by one-half unit distance each (easily seen by the rise of the trough of the loop by one-half of a grid length in FIG. 4).

Simultaneously, there is a strong Rack One distal-pull effect. Such an effect is symbolized in FIG. 4 by the arrow in the Rack One box representing left to right force applied to the clamps at point G holding the EXT-obturator during the cycle. The simultaneous force applied to the EXT-obturator creates a potentiating distal-pull effect; the two forces applied simultaneously accomplish the forward movement more easily. Importantly, the distal-pull effect additionally moves the leading end of the scope further into the bowel, and straightens out redundant and loose tortuous loops of the scope lying in the colon.

Figure 6:
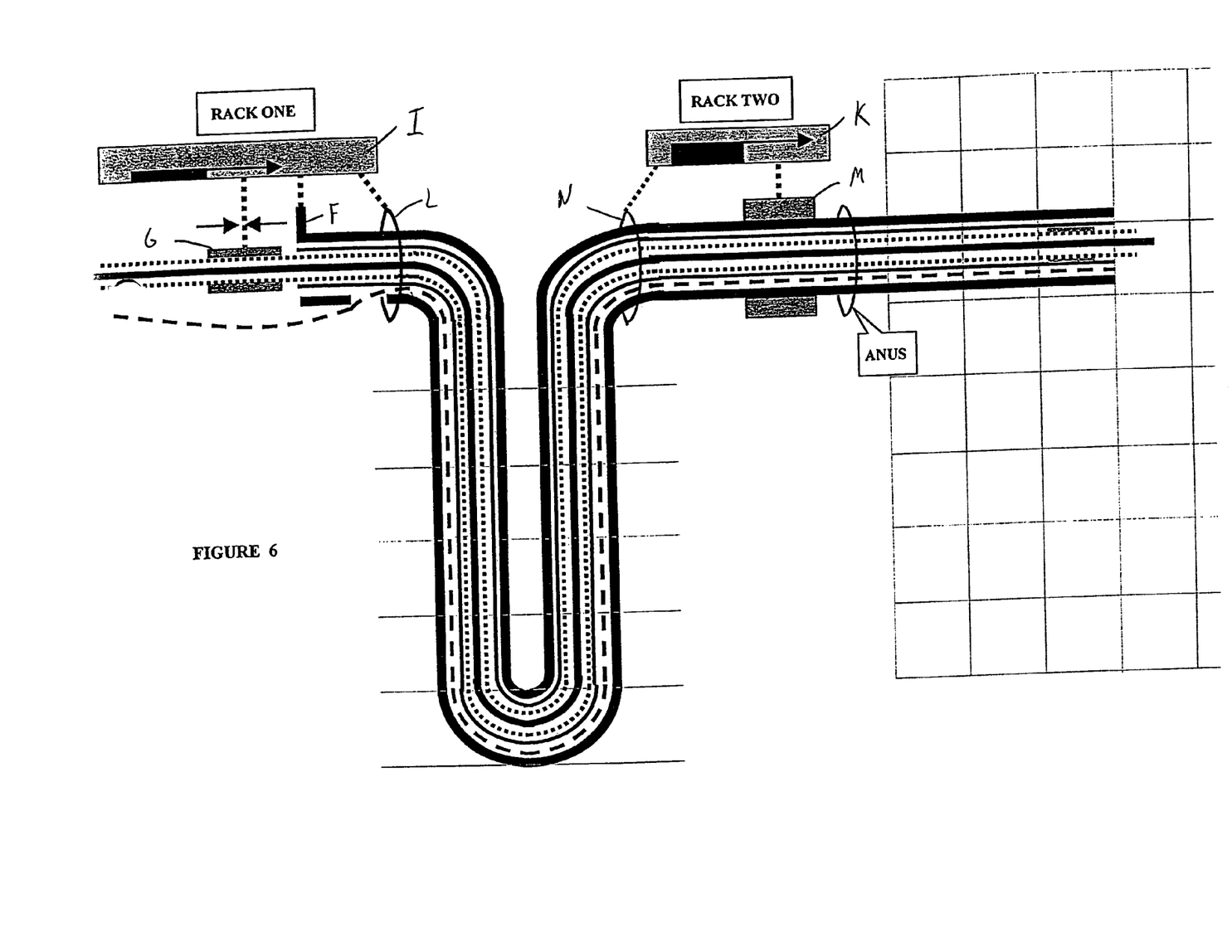
FIG. 6 is a side view in partial section of the system of FIG. 3 showing opposing forces acting upon the EXT-obturator of the system during a "proximal-push" and "distal-pull" cycle.

Next, consider one additional cycle of activity in which both the proximal-push effect of Rack Two and the distal-pull effect of Rack One are both strong. Comparison of FIG. 4 as the initial state prior to this second cycle with FIG. 6 as the end of the cycle, shows another unit distance advance of the scope, and additional shortening of both limbs of the scope's loop (FIG. 6). It is important to understand the interactions between the proximal-push and distal-pull mechanisms. Consider the consequences of strong constant force applied to move the EXT-obturator coupler of Rack One forward (i.e., to the right), symbolized by the left-to-right arrow applied to the coupler in FIG. 6. As the entire EXT-obturator is moved forward by this force, the entire distal segment of the endoscope to which it is integrally bound also moves to the right. Thus, this set of forces manifests the desired "distal-pull" effect on the distal end of the scope. Under the endoscopist's visual guidance and manipulation of the scopes tip's direction, the leading end of the scope is "pulled" into the open lumen pathway before it. The "distal-pull" effect of Rack One is simultaneous with and complementary to the "proximal-push" effect of Rack Two.

Further, consider the movement and spatial location of the EXT-obturator during this cycle ending as depicted in FIG. 6. During the cycle two opposing sets of forces act upon the sets of clamps at point G, represented by the two opposing arrows in FIG. 6. The first force, indicated by the left-to-right arrow, represents displacement to the right as left-to-right force is exerted on it to create the "distal-pull" effect. An opposing second set of forces (the right-to-left arrow) is dictated by the requirement that, at the end of each cycle, the spatial relationship of the EXT-obturator to the proximal end of the obturator channel must be the same as at the beginning of the cycle. This opposing set of forces tends to return the Rack One coupler toward its initial position. Briefly, the opposing forces can be explained as follows. At the end of cycle two, the combined Rack Two "proximal-push" and the Rack One "distal-pull" effects have moved the endoscope one unit distance into the patient. Because points F and M are fixed in space, the one unit length of the endoscope's advance into the patient in this cycle (seen by changes of position on the grid in FIG. 6) requires another shortening of both the descending and ascending limbs of the loop by one-half unit distance each. Since the length of the EXT-obturator (from point G proximally to its distal end) is constant, and its distal end is bonded to the distal end of the scope so that it cannot move beyond the distal end of the obturator channel, the shortening of the loop (driven by the proximal-push mechanism) forces the EXT-obturator coupling to return toward its original starting position. Because of the temporal coordination of the Rack Two proximal-push and the Rack One distal-pull effects, it is possible to greatly vary the amount of left-to right force applied to the EXT-obturator to obtain the desired distal-pull effect while causing only small amounts of displacement of the EXT-obturator coupler clamps. Thus, the mix of forces providing proximal-push and distal-pull effects can be varied greatly. The timing and magnitude of the two automated applied forces may be controlled by the endoscopist.

Generally speaking, the Rack Two effect has greater influence on moving the proximal segments of the scope, while the Rack One effect has greater influence on moving the distal segment of the scope. Returning to an earlier analogy, the Rack Two effect in isolation mimics the difficulty of trying to push a flexible rope from its proximal end. The combined Rack One and Rack Two effect is analogous to moving a rope by simultaneously moving its proximal and distal ends in a coordinated fashion. The proximal-push and the distal-pull mechanisms jointly contribute to the forward propelling motion: additionally, the distal-pull mechanism further advances the tip of the scope as it straightens tortuous and redundant curves of the scope in the colon.

During the cycle, the INT-obturator may be moved in and out manually and used for suction; or it may be removed and not used.

In some circumstances, the Rack One effect may be exerted alone. That is, the Rack Two proximal-push effect is not activated and simply holds the scope motionless at the point M location while forward pressure is exerted on the EXT-obturator coupling at point G to create a distal-pull effect. Such a maneuver further advances the tip of the scope by tightening loose and tortuous configurations of the scope relative to the bowel in which it lies between the anus and the distal tip of the scope.

Occasionally, this mechanism is used in reverse. In many circumstances, the endoscopist cannot identify the direction of the colon lumen; its appearance is confounded with cul-de-sacs or convolutions of loops of bowel segments. To address this problem, it is necessary to pull the endoscope partially out, and then explore during re-entry. By combining a static proximal-push mechanism (i.e., continuous anchoring of the scope at point M) with pulling or backward (i.e., right to left) movement of the proximal end of the EXT-obturator, the distal end of the EXT-obturator may be partially withdrawn, carrying with it the bonded distal segment of the endoscope. This avoids a major withdrawal by externally pulling the entire scope through the anus. It provides additional operational versatility to the colonoscopist for reaching the cecum.

The system illustrated in FIGS. 3–7 for automated propelling of an endoscope through the colon is based on the synergistic use of the two mechanisms described above. The first mechanism consists of repeated cycles, mediated through Rack Two, providing a "proximal-push" mechanism that progressively moves the endoscope through the anus into the colon. The duration of each cycle and the length of the segment of the endoscope moved forward in each cycle (hence, the linear rate of the scope's introduction into the patient) can be varied, and are under the control of the endoscopist. Additionally, the amount of Rack Two force applied in the cycles to effect the scope's forward movement through the anus is variable and controllable, so that sufficient but not excessive levels of force can be used.

The second mechanism, mediated through Rack One, provides for force applied to the proximal end of the EXT-obturator to be translated through the obturator channel and serve as a simulated "distal-pull" effect on the distal end of the scope. Rack One cycles are temporally coordinated with Rack Two cycles. In one of the examples described above, both proximal-push and distal-pull effects were strong. In another example described above, the distal-pull effects were used alone when the scope within the colon has loose, redundant tortuosities and curvatures that need to be straightened. The endoscopist can control the relative strengths of both methods used for propulsion. Given that the proximal-push has a predominant effect on the more proximal portion of the scope, and that the distal-pull has a more predominant effect on the distal portion of the scope, clinical experience will allow the endoscopist to vary the uses of the two mechanisms'characteristics at sequential stages of the procedure as he or she fashions the most effective use of these capabilities. The flexibility to do so is built into the system.

Figure 7:
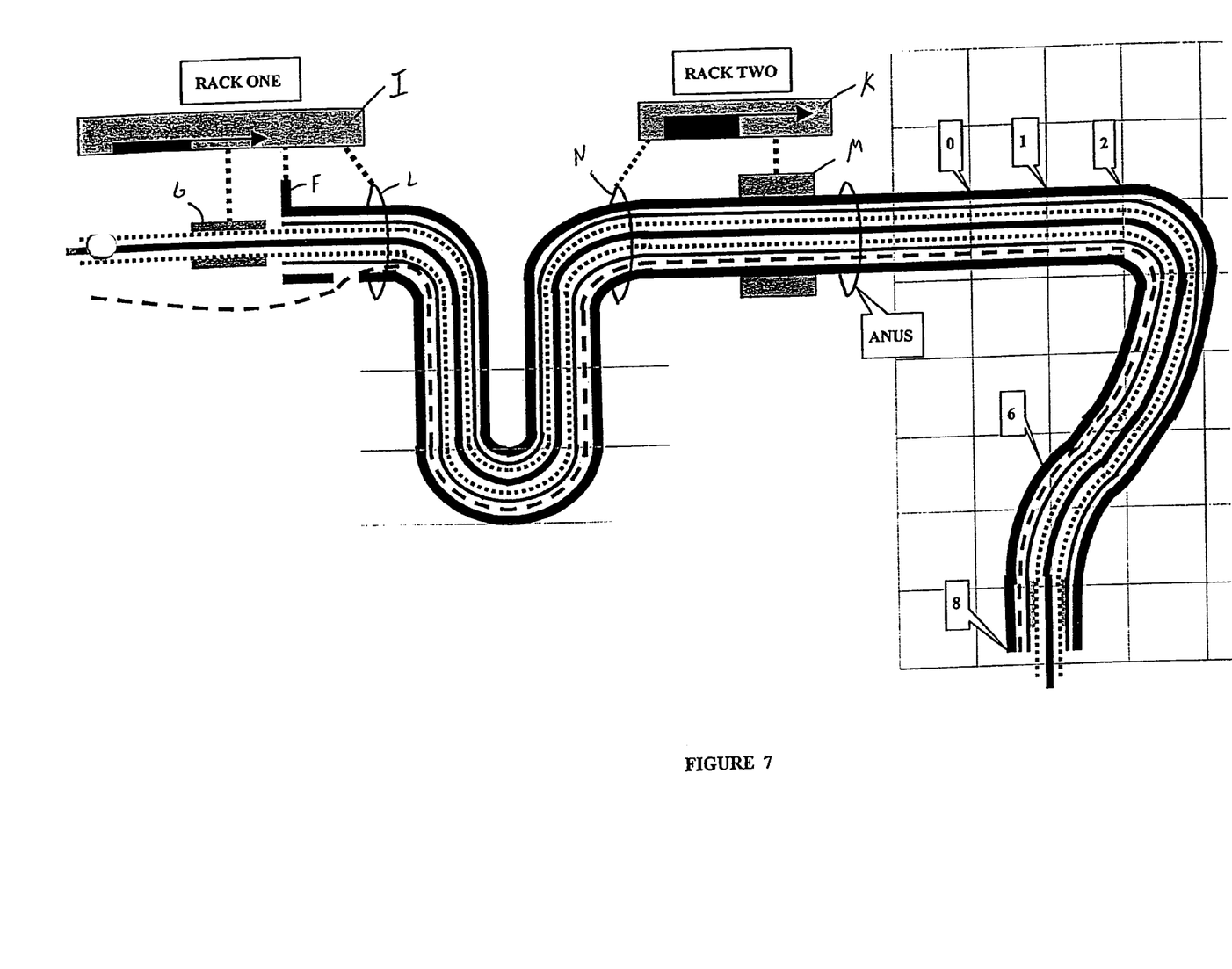
FIG. 7 is a side view in partial section of the system of FIG. 3 showing the configuration of the endoscope and obturators after eight cycles of movement by the system.

In FIGS. 3–7, two cycles of the proximal-push in combination with the distal-pull effects have been described. Repeating cycles in a manner described above allows the scope to traverse the colon from the rectosigmoid area to the cecum. In FIG. 7, a schematic illustration of the system is depicted after six additional cycles have occurred and the scope has negotiated curves to advance a total of 8 unit lengths. Points are labeled in FIG. 7 to depict the following travel path for the scope: "0" indicates where the end of the scope was at the point of the beginning of the first cycle; "1, 2, 6 and 8" indicate locations of the distal end of the scope after completion of corresponding automated propelling cycles. Each cycle results in one unit length progression of the distal end of the scope, indicated approximately as the distance between grid lines depicted in FIG. 7. Comparison of FIG. 3 (prior to the first automated cycle) with FIG. 7 (after completion of eight automated cycles) shows that the scope's forward progression of eight unit lengths through the colon occurs at the expense of the loop whose descending and ascending limbs each are four unit lengths shorter.

Of critical importance is the system's behavior as the leading tip of the endoscope approaches curved loops of colon. As the endoscopist visualizes such curves, the direction of the tip of the scope is manipulated so that its linear axis lines up with the linear axis of the gut lumen immediately ahead of it. Since the effective site of the distal-pull effect is very close to the terminal end of the scope, its thrust should support forward movements of the scope into the lumen opening ahead of it; repeated small steps may be needed to negotiate severe curves. The resistance of the bowel wall to deformation may be recruited to help guide the scope around such curves. Additional cycles add to the progression of the endoscope, until it reaches the cecal area. Once reached, the endoscopist can disengage the automated propelling system, and revert to the customary procedures for examination of the colon as the colonoscope is manually withdrawn. As it is withdrawn, the obturator channel is available for insertion of any of the diagnostic or therapeutic tools needed as determined by the endoscopist's findings.

It is important to avoid application of excessive forces. Since movement of the endoscope is largely effected by means of force exerted through Rack One and Rack Two motors, mechanisms may be instituted to prevent excessive force being exerted on the colon. For example, pressure sensors on the leading tip of the endoscope and/or of the obturators can be programmed to alarm the operator, and to interrupt continuation of the propelling mechanism when specified pressure levels are exceeded.

Figure 8A:
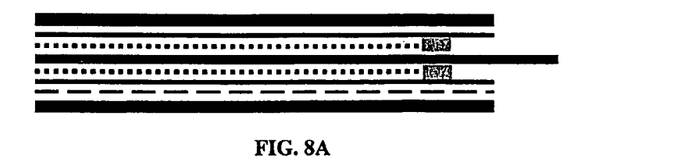
FIGS. 8A–8F are views in partial section of alternative embodiments of a self-propelling endoscope system according to the present invention.

Several alternative technologies to support the "distal-pull" effect are illustrated in FIGS. 8A–8F. In FIG. 8A, the releasable bonding mechanism J includes a retractable flange that is extruded from the distal wall of the obturator channel into the lumen against which the EXT-obturator abuts. Forward or left-to-right force applied to the proximal EXT-obturator coupling is translated to, and moves the distal tip of the scope forward. Creating the retractable flange entails engineering changes of the colonoscope.

Figure 8B:
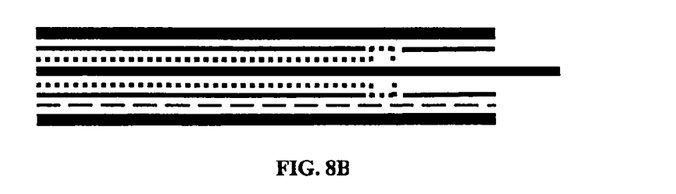

In FIG. 8B, a gap in the distal wall of the obturator channel serves as a receptor for a stent-like protrusion from the distal end of the EXT-obturator. The stent-like protrusion can be controlled by the endoscopist to engage the gap and thus serves as the releasable bonding mechanism J and a functional alternative to the retractable flange of FIG. 8A.

Figure 8C:
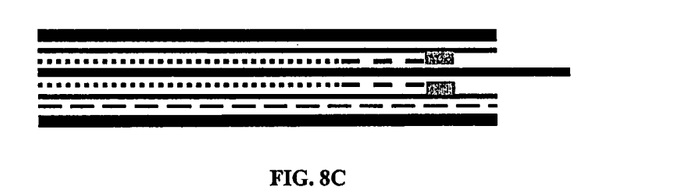

In FIG. 8C, the releasable bonding mechanism J includes a tip on the EXT-obturator that abuts extruded flanges in the distal obturator channel. Alternative force mechanisms can also be used. For example, once the tip of the EXT-obturator is abutted to the retractable flanges, the tip of the EXT-obturator can have force applied via an expandable section (i.e., the large dashed extension depicted in FIG. 8C) controlled from the outside by the endoscopist. The force exerted could be from an electronically controlled solenoid or linear activator; or from high-pressure injection of gas or water through a fine tube running the length of the obturator.

Figure 8D:
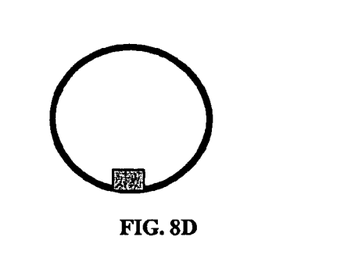

FIG. 8D depicts a semilunar or rectangular shaped metal flap which is installed on the leading edge of the scope and serves as the releasable bonding mechanism J and a substitute for the retractable flange of FIG. 8A. Its position would line up directly with a dedicated obturator lumen, so that the transmission of force function of the EXT-obturator would be exerted directly on it. It could be small enough so that there would be no compromise of other needed endoscopic functions.

Figure 8E:
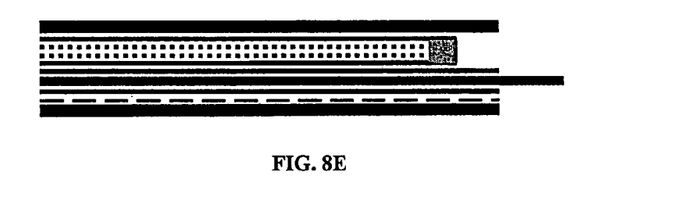

Separate channels can also be used for the EXT-obturator and INT-obturator functions. As illustrated in FIG. 8E, one channel would be used for suction (via the INT-obturator) and a second dead-end channel would be used for the force translation effects from the EXT-obturator.

Figure 8F:
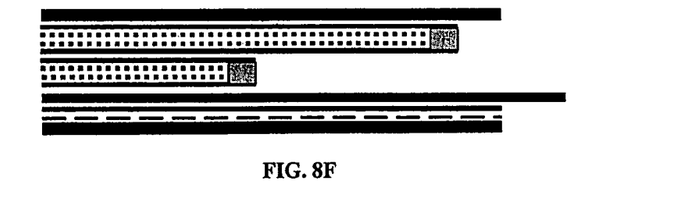

For very long scopes (e.g., the enteroscope), three channels could be used to add a mid-scope distal pull effect such as the scope depicted in FIG. 8F. Separate channels could be used for the EXT-obturator and INT-obturator functions. As shown, one channel would be used for suction (via the INT-obturator), a second dead-end channel would be used for the force translation effects from the EXT-obturator on the distal end of the scope, and a third channel that was dead-ended at mid-distance from the two ends of the scope would be used for an additional EXT-obturator for force translation effects on the middle section of the scope. (For the mid-scope effect to succeed, the dead-end of that channel needs to be directly bonded to the external scope wall to mediate the distal-pull effect.)

The systems of the present invention are not limited to endoscopes for use in the colon; rather, the systems described above are also relevant to enteroscopes and to endoscopes for examination of other tubular organs and structures. For example, the mechanisms described above for the colonoscope can be, with some minor modifications, translated directly into use for automated rapid propelling of an enteroscope through the stomach, duodenum, jejunum and ileum. Its potential for improving diagnostic and therapeutic approaches to the small bowel is clear. Miniaturized versions of the propelling mechanism of the present invention can be useful for advancing small catheters into: the gall bladder and hepato-biliary ducts; pancreatic ducts; ureters and kidneys; uterus and Fallopian tubes; and blood vessels of many organs. Enlarged versions of the propelling mechanism can be useful for non-medical applications such as advancing non-rigid instruments to identify and remedy disturbances of plumbing and fluid pumping systems, etc.

Having described preferred embodiments of a new and improved automated self-propelling endoscope, it is believed that other modifications, variations and changes will be suggested to those skilled in the art in view of the teachings set forth herein. It is therefore to be understood that all such variations, modifications and changes are believed to fall within the scope of the present invention as defined by the appended claims. Although specific terms are employed herein, they are used in a generic and descriptive sense only and not for purposes of limitation.

What is claimed is:

1. A system for self-propelling a colonoscope within an intestine comprising:
   a scope housing;
   an obturator channel disposed within and extending between proximal and distal ends of the scope housing, wherein the obturator channel is secured to the scope housing such that movement of the obturator channel effects movement of the scope housing;
   an obturator disposed within the obturator channel and extending beyond the proximal end of the scope housing, wherein the obturator is secured to a section of the obturator channel at a securing location proximate the distal end of the scope housing;
   a bonding mechanism to releasably secure the obturator to the obturator channel section: and
   a pull control device coupled to the obturator at a coupling location proximate the proximal end of the scope housing, wherein the pull control device is configured to apply a force upon the obturator at the coupling location to effect application of a corresponding pulling force on the obturator channel at the securing location and the distal end of the scope housing resulting in a corresponding movement of the distal end of the scope housing into the intestine that increases an intestinal path distance between the distal end of the scope housing and an insertion point of the scope housing into the intestine.

2. The system of claim 1, wherein the pull control device is further configured to control the force applied to the obturator to effect corresponding movement of the distal end of the scope housing in a direction that decreases the intestinal path distance between the distal end of the scope housing and the insertion point.

3. The system of claim 1, wherein the bonding mechanism includes an inflatable balloon surrounding an outer surface of the obturator.

4. The system of claim 1, further comprising:
   an internal obturator insertable and extendable between proximal and distal ends of the obturator; and
   a fiberoptic channel disposed within and extending between the proximal and distal ends of the scope housing.

5. The system of claim 1, further comprising:
   a push control device coupled to the scope housing a selected distance from the proximal end of the scope housing, wherein the push control device is configured to apply a pushing force to the scope housing in a direction corresponding to the force applied to the obturator by the pull control device.

6. The system of claim 5, wherein the system prevents any movement of the proximal end of the scope housing in response to the forces applied by the push and pull control devices, the scope housing includes a looped section situated between the push and pull control devices, and the looped section of the scope housing decreases in length as the intestinal path distance between the distal end of the scope housing and the insertion point is increased.

7. The colonoscope of claim 6, wherein each of the push and pull control devices includes a supporting ring configured to support an end of the looped section such that the scope housing is maintained at a desired position in relation to the push and pull control devices.

8. The colonoscope of claim 5, wherein the pull control device includes a clamping element movable in relation to the pull control device and configured to releasably secure to the obturator, the push control device includes a clamping element movable in relation to the push control device and configured to releasably secure to the scope housing, and each of the push and pull control devices is further configured to control movement and securement of the respective clamping device so as to effect application of a respective one of the pushing and pulling forces.

9. The colonoscope of claim 8, wherein each clamping element of the push and pull control devices includes a first pair of opposing clamps and a second pair of opposing clamps spatially offset from the first pair of opposing clamps, and each of the push and pull control devices is further configured to selectively alternate control of movement and securement between the respective first pair of opposing clamps and the respective second pair of opposing clamps to effect application of the respective one of the pushing and pulling forces.

10. A system for propelling a hollow probing member through a tunnel, wherein the probing member includes an internal member disposed within and protruding from a proximal end of the probing member, the internal member being releasably secured via a bonding mechanism to an internal section of the probing member at a securing location proximate a distal end of the probing member, the system comprising:
    a pull control device including a coupling member securable to the internal member at a coupling location proximate the proximal end of the probing member, wherein the pull control device is configured to apply a force to the internal member at the coupling location to effect application of a pulling force at the distal end of the probing member resulting in a corresponding movement of the distal end of the probing member into the tunnel that increases a tunnel path distance between the distal end of the probing member and an insertion point of the probing member into the tunnel.

11. The system of claim 10, wherein the pull control device is further configured to control the force applied to the internal member to effect corresponding movement of the distal end of the probing member in a direction that decreases the tunnel path distance between the distal end of the probing member and the insertion point.

12. The system of claim 10, further comprising:
    a push control device including a coupling member securable to the probing member, wherein the push control device is configured to apply a pushing force to the probing member in a direction corresponding to the pulling force applied to the distal end of the probing member by the pull control device.

13. The system of claim 12, wherein each of the push and pull control devices includes a supporting ring configured to support a portion of the probing member to maintain at a desired position of the probing member in relation to the push and pull control devices.

14. The system of claim 12, wherein the pull control device includes a clamping element movable in relation to the pull control device and configured to releasably secure to the internal member, the push control device includes a clamping element movable in relation to the push control device and configured to releasably secure to the probing member, and each of the push and pull control devices is further configured to control movement and securement of the respective clamping device so as to effect application of a respective one of the pushing and pulling forces.

15. The system of claim 14, wherein each clamping element of the push and pull control devices includes a first pair of opposing clamps and a second pair of opposing clamps spatially offset from the first pair of opposing clamps, and each of the push and pull control devices is further configured to selectively alternate control of movement and securement between the respective first pair of opposing clamps and the respective second pair of opposing clamps to effect application of the respective one of the pushing and pulling forces.

16. The system of claim 10, wherein the probing member is a colonoscope, the internal member is an obturator, and the coupling member of the pull control device is securable to the obturator.

17. A method for propelling a colonoscope within an intestine of a subject, wherein the colonoscope includes a scope housing, an obturator channel disposed within and extending between proximal and distal ends of the scope housing, the obturator channel being secured to the scope housing such that movement of the obturator channel effects movement of the scope housing, and an obturator disposed within the obturator channel and extending beyond the proximal end of the scope housing, the obturator being releasably secured, via a bonding mechanism, to a section of the obturator channel at a securing location proximate the distal end of the scope housing, the method comprising:
(a) inserting the distal end of the scope housing into the intestine of the subject at a selected insertion point; and
(b) applying a force to the obturator at a location proximate the proximal end of the scope housing to effect a corresponding pulling force on the obturator channel at the securing location and the distal end of the scope housing, wherein the pulling force results in a corresponding movement of the distal end of the scope housing within the intestine that increases or decreases an intestinal path distance between the distal end of the scope housing and the insertion point.

18. The method of claim 17, further comprising:
(c) applying a force to the scope housing at a selected distance from the proximal end of the scope housing and in a direction corresponding to the force applied to the obturator.

19. The method of claim 18, wherein (b) includes:
(b.1) automatically applying the force to the obturator via a pull control device coupled to the obturator at the location proximate the proximal end of the scope housing; and
wherein (c) includes:
(c.1) automatically applying the force to the scope housing via a push control device coupled to the scope housing at the selected distance from the proximal end of the scope housing.

20. The method of claim 19, wherein the scope housing includes a looped section disposed between the push and pull control devices, and the method further comprises:
(d) preventing any movement of the proximal end of the scope housing in response to forces applied by the push and pull control devices in (b.1) and (c.1) such that, when the distal end of the scope housing is moved in a direction that increases the intestinal path distance between the distal end of the scope housing and the insertion point, the looped section decreases in length.

21. The method of claim 20, further comprising:
(e) supporting a first end of the looped section of the scope housing via a first ring coupled to the pull control device, wherein the first end extends through the first ring; and
(f) supporting a second end of the looped section of the scope housing via a second ring coupled to the push control device, wherein the second end extends through the second ring.

22. The method of claim 19, wherein each of the push and pull control devices includes a first and second pair of clamps to control the forces applied to the obturator and the scope housing, wherein each pair of clamps is movable with respect to a respective one of the push and pull control devices and is releasably securable to a respective one of the obturator and the scope housing; and
wherein (b.1) includes:
(b.1.1) alternating control between the first pair of clamps and the second pair of clamps of the pull control device to apply the respective force to the obturator; and
wherein (b.2) includes:
(b.2.1) alternating control between the first pair of clamps and the second pair of clamps of the push control device to apply the respective force to the scope housing.

23. A system for self-propelling a colonoscope within an intestine, the colonoscope including a scope housing and an obturator extending within and protruding from a proximal end of the scope housing, the obturator being releasably secured, via a bonding mechanism, to the scope housing at a location proximate the distal end of the scope housing, the system comprising:
a means for applying a force to the obturator at the proximal end of the scope housing that effects a pulling movement of the distal end of the scope housing in a direction toward or away from an insertion point of the scope housing within the intestine.

24. The system of claim 23, further comprising:
a means for applying a force to the scope housing in a direction that corresponds to the force applied to the obturator.

25. A system for self-propelling a colonoscope within an intestine comprising:
a scope housing;
an obturator channel disposed within and extending between proximal and distal ends of the scope housing, wherein the obturator channel is secured to the scope housing such that movement of the obturator channel effects movement of the scope housing;
an obturator disposed within the obturator channel and extending beyond the proximal end of the scope housing, wherein the obturator is secured to a section of the obturator channel at a securing location proximate the distal end of the scope housing;
an internal obturator insertable and extendable between proximal and distal ends of the obturator; and
a fiberoptic channel disposed within and extending between the proximal and distal ends of the scope housing; and
a pull control device coupled to the obturator at a coupling location proximate the proximal end of the scope housing, wherein the pull control device is configured to apply a force upon the obturator at the coupling location to effect application of a corresponding pulling force on the obturator channel at the securing location and the distal end of the scope housing resulting in a corresponding movement of the distal end of the scope housing into the intestine that increases an intestinal path distance between the distal end of the scope housing and an insertion point of the scope housing into the intestine.

26. The system of claim 5, wherein the scope housing includes a looped section situated between the push and pull control devices, and the proximal end of the scope housing and the looped section of the scope housing are suitably anchored to control the length of the looped section such that there is no increase in the length of the looped section when forces are applied by the push and pull control devices.

27. The method of claim 19, wherein the scope housing includes a looped section disposed between the push and pull control devices, and the method further comprises:
(d) suitably anchoring the proximal end of the scope housing and the looped section to prevent any increase in the length of the looped section when forces are applied by the push and pull control devices in (b.1) and (c.1).

* * * * *